(12) United States Patent
Finke

(10) Patent No.: US 8,672,878 B2
(45) Date of Patent: Mar. 18, 2014

(54) BUFFERING AGENT DELIVERY SYSTEM FOR ANESTHETIC SYRINGE

(75) Inventor: Melvin A. Finke, DeLand, FL (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 13/438,856

(22) Filed: Apr. 4, 2012

(65) Prior Publication Data

US 2012/0259279 A1   Oct. 11, 2012

Related U.S. Application Data

(60) Provisional application No. 61/471,913, filed on Apr. 5, 2011.

(51) Int. Cl.
*A61M 5/315* (2006.01)

(52) U.S. Cl.
USPC ................................ 604/87; 604/82; 604/86

(58) Field of Classification Search
CPC ........................................................ A61M 5/315
USPC ............................................... 604/82, 86–88
See application file for complete search history.

(56) References Cited

U.S. PATENT DOCUMENTS

| | | | |
|---|---|---|---|
| 1,661,818 A | | 3/1928 | Cook |
| 2,869,542 A | | 1/1959 | Orsten et al. |
| 3,684,136 A | * | 8/1972 | Baumann ........................ 222/386 |
| 4,767,413 A | * | 8/1988 | Haber et al. .................... 604/198 |
| 5,354,285 A | | 10/1994 | Mazurik et al. |
| 5,603,695 A | * | 2/1997 | Erickson .......................... 604/89 |
| 5,637,087 A | * | 6/1997 | O'Neil et al. ..................... 604/82 |
| 6,080,132 A | * | 6/2000 | Cole et al. ........................ 604/85 |
| 7,329,235 B2 | * | 2/2008 | Bertron et al. ................... 604/88 |

(Continued)

FOREIGN PATENT DOCUMENTS

| | | |
|---|---|---|
| GB | 787 963 A | 12/1957 |
| GB | 2 455 228 A | 7/2008 |
| JP | 63-290577 A | 11/1988 |
| JP | 5-237195 A | 9/1993 |

OTHER PUBLICATIONS

European Search Report dated Jul. 30, 2012 from European Application No. 12162969.5, 6 pages.

(Continued)

*Primary Examiner* — Nicholas Lucchesi
*Assistant Examiner* — Gerald Landry, II
(74) *Attorney, Agent, or Firm* — Lisa E. Winsor, Esq.

(57) ABSTRACT

A syringe for dispensing anesthetic from a cartridge having an interior wall defining a hollow interior sized and shaped for receiving a dose of anesthetic, and a piston. The syringe includes a tubular plunger slidably received in the hollow interior of the tubular cartridge. The plunger has a hollow interior extending between a distal end shaped for engaging the piston and an open proximal end. The syringe includes a plunger rod slidably received in the hollow interior of the tubular plunger. The rod has a sharp distal end adapted to penetrate the piston, a proximal end, and a length extending between the distal end and the proximal end sized so a delivery portion of the rod extends through the piston into the cartridge when the rod is driven through the piston. The delivery portion includes a recess for receiving a buffering agent to reduce acidity of the dose of anesthetic.

6 Claims, 4 Drawing Sheets

(56) References Cited

U.S. PATENT DOCUMENTS

| | | | |
|---|---|---|---|
| 8,251,958 B2* | 8/2012 | Sullivan et al. | 604/232 |
| 2004/0092883 A1* | 5/2004 | Casey et al. | 604/191 |
| 2004/0236212 A1 | 11/2004 | Jones et al. | |
| 2006/0052747 A1* | 3/2006 | Nishimura et al. | 604/85 |
| 2008/0171971 A1* | 7/2008 | DiPerna et al. | 604/82 |
| 2011/0092906 A1* | 4/2011 | Bottger et al. | 604/143 |
| 2012/0172793 A1* | 7/2012 | Cronenberg et al. | 604/87 |

OTHER PUBLICATIONS

English Translation of Notice of Reasons for Rejection issued May 13, 2013 in corresponding Japanese Patent Application No. 2012-85534, 4 pages.

Office Action dated Sep. 9, 2013 regarding Canadian Patent Application No. 2773480, 3 pages.

* cited by examiner

BUFFERING AGENT DELIVERY SYSTEM FOR ANESTHETIC SYRINGE

CROSS REFERENCE TO RELATED APPLICATION

This application claims priority to U.S. Patent Application 61/471,913 filed Apr. 5, 2011, which is hereby incorporated by reference in its entirety.

BACKGROUND

The present invention generally relates to syringes for injecting liquid medications from prefilled cartridges, and more particularly to a syringe having a buffering agent delivery system for reducing the acidity of anesthetic.

Local anesthetic is frequently used to numb tissue in a patient's mouth to reduce pain and discomfort a patient may feel during a dental procedure. Conventionally, a reusable syringe assembly is used to inject the anesthetic or medicine from a cartridge or carpule. The cartridge is a glass cylinder containing a local anesthetic and other ingredients. A diaphragm at one end of the cylinder is held in place by an aluminum band. The opposite end of the cylinder has a moveable piston or stopper. The syringe assembly includes a barrel for receiving the cartridge, a plunger rod slidably received in a proximal end of the barrel for actuating the cartridge, an access needle at a distal end of the barrel for puncturing the diaphragm, and a delivery needle connected to the access needle for delivering anesthetic to the patient. In some cases, the plunger rod includes a harpoon for engaging the piston.

Typically, the diaphragm of the cartridge is swabbed with alcohol before being loaded into a pre-sterilized syringe. As the cartridge is loaded into the syringe, the access needle extending proximally from the distal end of the barrel pierces the cartridge diaphragm so the anesthetic in the cartridge can be dispensed. Once the cartridge is in place, the plunger rod of the syringe pushes the piston of the cartridge toward the diaphragm, forcing anesthetic through the access needle, into the delivery needle, and ultimately into the patient.

Frequently, a topical anesthetic is used to reduce pain caused by the entry of the needle into the tissue and the delivery of the medicine. Among the properties that make anesthetic delivery painful is its acidity. Local anesthetic solutions containing vasopressors (e.g., epinephrine) are intentionally manufactured with lower pH (3-4 pH) to slow the oxidation of the vasopressor prolonging its effectiveness and thereby extending the shelf life of the drug. Thus, there is a need for a device that delivers effective anesthetic having a reduced acidity, without affecting the shelf life of the drug.

The present invention relates to a dental syringe for dispensing anesthetic from a cartridge having an interior wall defining a hollow interior sized and shaped for receiving a dose of anesthetic, and a piston. The syringe comprises a tubular plunger slidably received in the hollow interior of the tubular barrel. The plunger has a hollow interior extending between a distal end shaped for engaging the piston and an open proximal end opposite the distal end. In addition, the syringe includes a plunger rod slidably received in the hollow interior of the tubular plunger. The rod has a sharp distal end adapted to penetrate the seal, a proximal end, and a length extending between the distal end and the proximal end sized so that a delivery portion of the rod extends through the piston into the cartridge when the rod is driven through the piston. The delivery portion includes a recess for receiving a buffering agent to reduce an acidity of the dose of anesthetic.

SUMMARY

In one aspect, the present invention includes a syringe for dispensing anesthetic from a cartridge having an interior wall defining a hollow interior sized and shaped for receiving a dose of anesthetic, and a piston. The syringe comprises a tubular plunger slidably received in the hollow interior of the tubular cartridge. The plunger has a hollow interior extending between a distal end shaped for engaging the piston and an open proximal end opposite the distal end. The syringe has a plunger rod slidably received in the hollow interior of the tubular plunger. The rod has a sharp distal end adapted to penetrate the piston, a proximal end, and a length extending between the distal end and the proximal end sized so that a delivery portion of the rod extends through the piston into the cartridge when the rod is driven through the piston. The delivery portion includes a recess for receiving a buffering agent to reduce an acidity of the dose of anesthetic.

In another aspect, the present invention includes a syringe and cartridge system comprising a cartridge having an interior wall defining a hollow interior sized and shaped for receiving a dose of anesthetic, and a piston slidably engaging the interior wall. The piston has a distal face facing the dose of anesthetic in the hollow interior of the cartridge, a proximal face opposite the distal face, a recess in the proximal face for receiving a predetermined amount of buffering agent, and a sheet sealing the buffering agent in the recess. The syringe and cartridge system also includes a plunger rod having a sharp distal end adapted to penetrate the sheet and piston forming a hole through the piston, the buffering agent entering the hollow interior of the cartridge to reduce acidity of the dose of anesthetic therein.

Other aspects of the present invention will be apparent in view of the following description and claims.

BRIEF DESCRIPTION OF THE DRAWINGS

Corresponding reference characters indicate corresponding parts throughout the drawings.

DETAILED DESCRIPTION OF THE DRAWINGS

Figure 1:
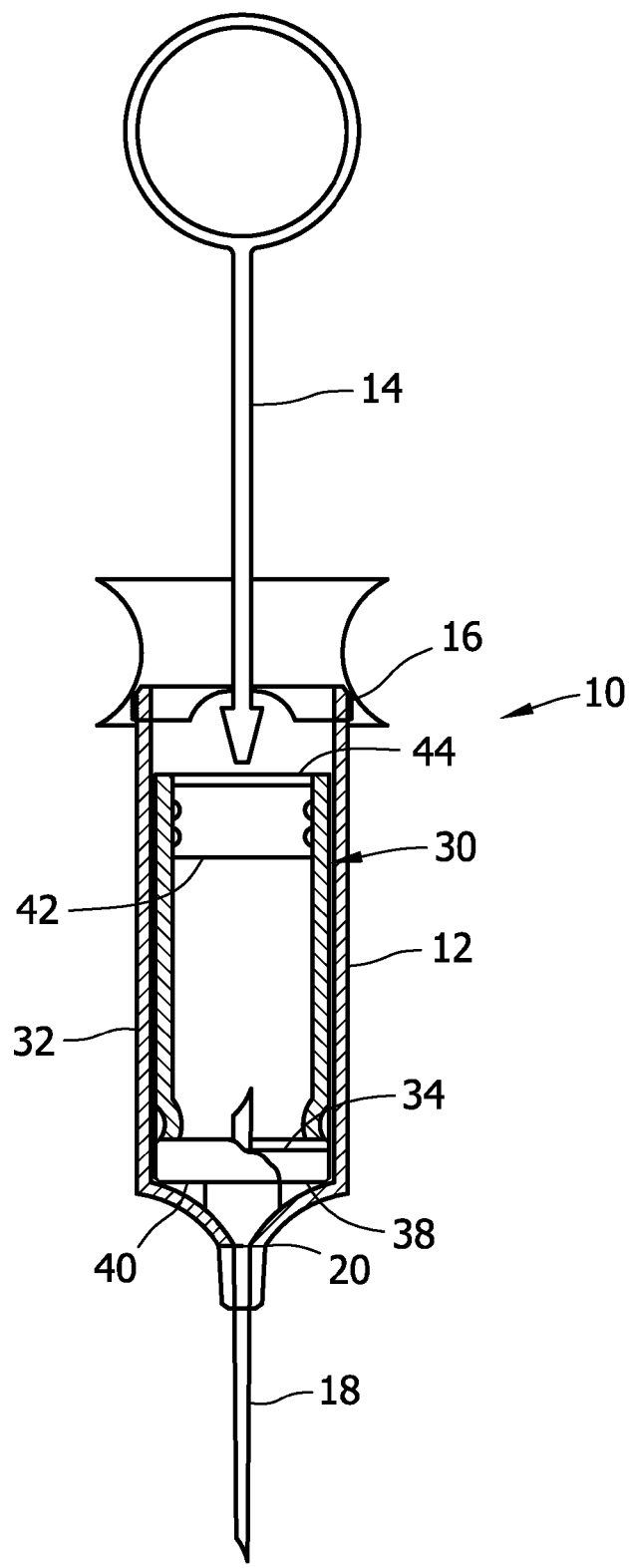
FIG. 1 is a side elevation in partial section of a syringe of the present invention.

Referring to FIG. 1, a dental syringe of a first embodiment of the present invention is generally designated in its entirety by the reference number 10. The dental syringe 10 generally comprises a tubular barrel 12 and a plunger rod 14 slidably received in a head or proximal end 16 of the barrel. A needle 18 is connected to an outlet 20 of the syringe at its distal end for dispensing anesthetic to tissue of a patient when the plunger rod 14 is forced distal.

A cartridge or carpule, generally designated by 30, loaded in a hollow interior of the syringe barrel 12 holds the anesthetic before being dispensed. The cartridge 30 includes a transparent cylinder 32 having a elastomeric diaphragm 34 held in place at its distal end 38 by a band 40, and an elastomeric stopper or piston 42 positioned in a proximal end 44 of the cylinder 32. The diaphragm 34 is pierced to put the anesthetic in communication with the dispensing needle 18 of the syringe 10. The plunger rod 14 of the syringe 10 engages the piston 42 and forces the anesthetic out of the cylinder 32 and through the dispensing needle 18.

Figure 2A:
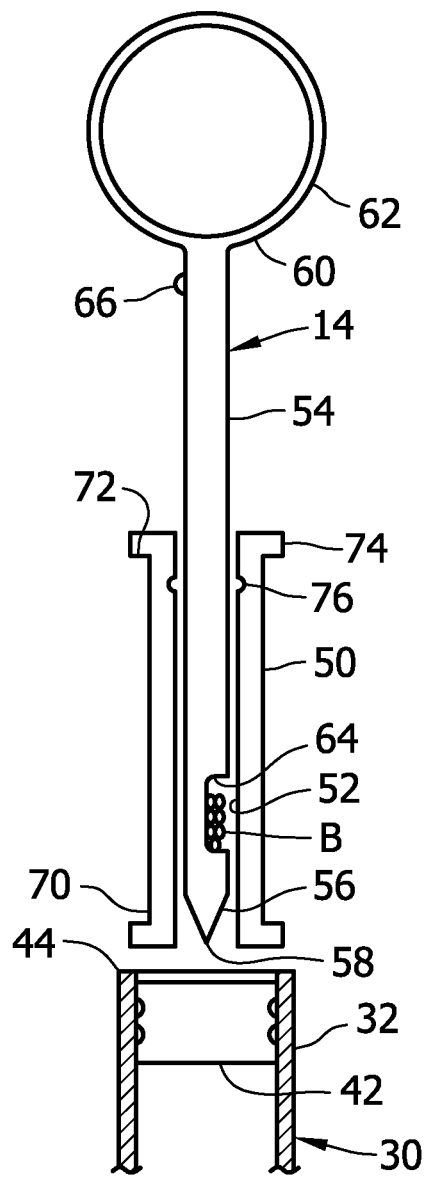
FIG. 2a is a cross section of a plunger rod of a first embodiment of the present invention prior to delivering buffering agent to a cartridge.

As illustrated in FIG. 2a, the plunger rod 14 includes a tubular plunger or guide 50 having a channel 52 that slideably receives a rod 54. A distal end 56 of the rod 54 includes a sharp point 58 for penetrating the piston 42 of the cartridge 30 as will be explained in more detail below. A proximal end 60 of the rod 54 includes a conventional thumb ring 62 for driving the rod through the cartridge piston 42. A cavity 64 is provided in the rod 54 near its distal end 56 for holding a buffering agent B prior to delivering it to the cartridge. A detent 66 is provided on the rod 54 near the thumb ring 62 for connecting the rod 54 to the guide 50 so they move in unison.

The distal end of the guide 50 includes a flange 70 sized for receipt in the proximal end 44 of the cartridge 30 to center the rod 54 on the piston 42. A proximal end 72 of the guide 50 also includes a flange 74 for centering the guide in the syringe barrel 12. A groove 76 is provided around the channel 52 adjacent the proximal end 72 for receiving the detent 66 on the rod 54 to prevent movement between the rod and the guide 50.

Figure 2B:
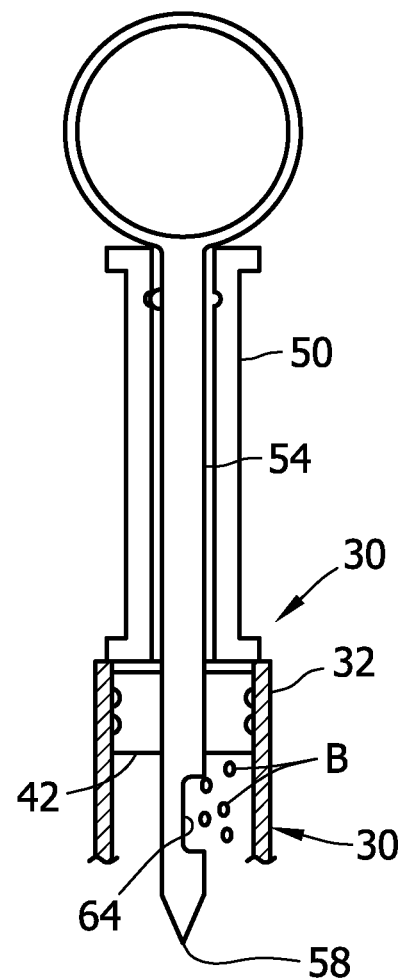
FIG. 2b is a cross section of the plunger rod of a first embodiment after delivering buffering agent to the cartridge.

As will be appreciated by those skilled in the art, when the rod 54 is initially advanced, the rod moves distally inside the guide 50 so the sharp point 58 pierces the piston 42 of the cartridge 30. As the rod 54 advances farther, the cavity 64 enters the hollow interior of the cartridge 30 as shown in FIG. 2b so the buffering agent B mixes with the anesthetic in the cartridge, reducing the acidity of the anesthetic. Eventually, the detent 66 on the rod 54 engages the groove 76 in the channel 52 of the guide 50 so the guide advances with the rod. As the guide 50 advances, it forces the piston 42 of the cartridge 30 distally in the cylinder 32, dispensing the contents of the cartridge through a needle extending through the diaphragm 34 of the cartridge. In addition, the detent 66 permits the piston 42 to be retracted by pulling back on the thumb ring 62 to aspirate anesthetic from the tissue as will be appreciated by those skilled in the art. In another embodiment, the anesthetic in the cartridge 30 may be at a negative pressure (i.e., a partial vacuum) to allow the buffer in the rod to easily exit the rod and mix with the anesthetic in the cartridge.

Figure 3:
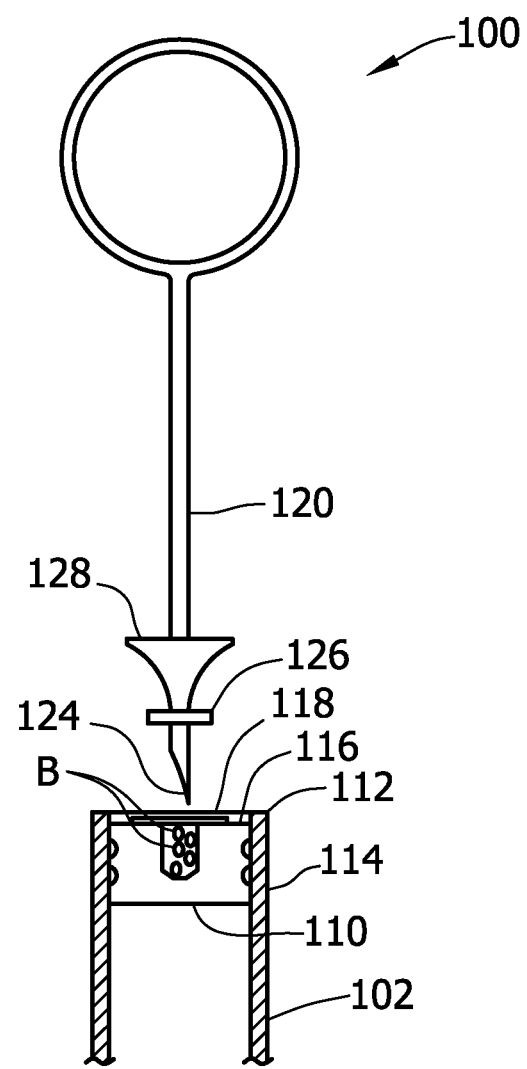
FIG. 3 is a cross section of a plunger rod and cartridge system of a second embodiment.

FIG. 3 illustrates another embodiment of a cartridge, generally designated by 100. The cartridge 100 includes a transparent cylinder 102 having an elastomeric diaphragm (not shown) held in place at its distal end by a band (not shown), and an elastomeric piston 110 positioned in a proximal end 112 of the cylinder 102. The piston 110 includes a cavity 114 in its proximal face 116. The cavity 114 is filled with buffering agent B and covered with a film 118 to retain the agent in the cavity. As further illustrated in FIG. 3, a plunger rod 120 of the second embodiment has a sharp point 124 for penetrating the film 118 and the piston 110. The rod 120 also includes a flange 126 immediately proximal to the sharp point 124 and a second larger flange or barb 128 positioned proximal to the first flange.

As will be appreciated by those skilled in the art, when the plunger rod 120 is initially advanced, the rod moves distally so its sharp point 124 pierces the film 118. Moving farther, the sharp point 124 of the rod 120 pierces the piston 110. As the rod 120 is advanced still farther, the first flange 126 pushes the buffering agent B through the opening in the piston 110 created by the sharp point 124. As in the first embodiment, the buffering agent B reduces the acidity of the anesthetic. Advancing the rod 120 still farther engages the barb 128 with the piston 110, forcing it distally in the cylinder 102 to dispense the contents of the cartridge through a needle extending through the diaphragm (not shown) of the cartridge 100. The barb 128 permits the piston 110 to be withdrawn, aspirating the tissue.

Figure 4:
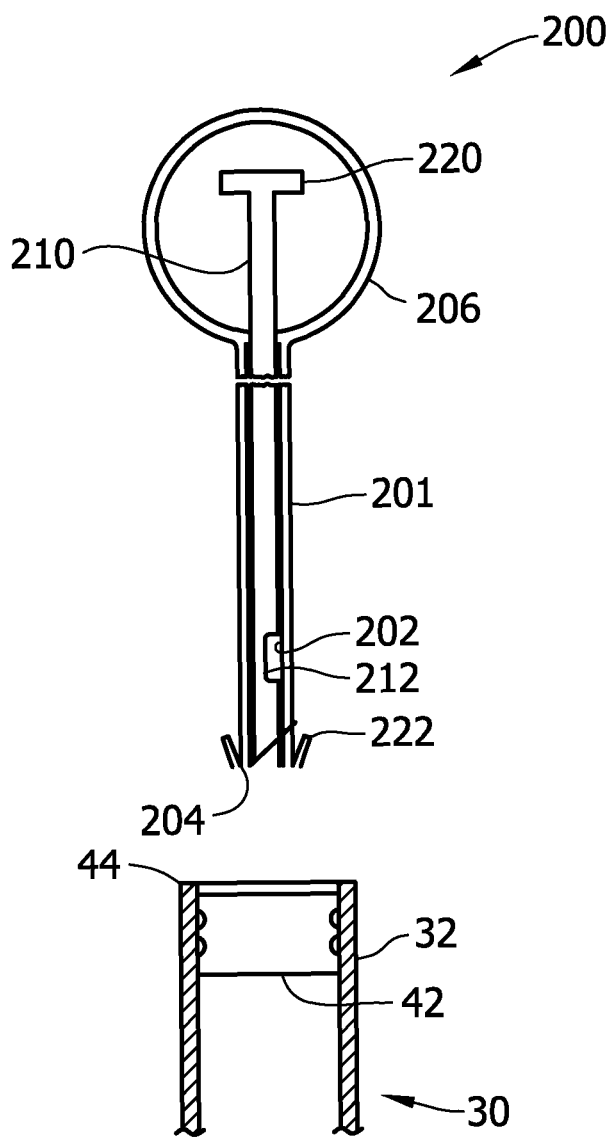
FIG. 4 is a cross section of a plunger rod of a third embodiment.

In a third embodiment illustrated in FIG. 4, a buffer delivery system 200 comprises a tubular plunger 201 having a channel 202 extending between a sharp point 204 at its distal end and a thumb ring 206 at its proximal end. A rod 210 having a cavity 212 extends through the channel 202. When the tubular plunger 201 is initially advanced, its sharp point 204 pierces the piston 42. Once the piston 42 is pierced, the rod 210 is advanced until the cavity 212 enters the interior of the cylinder 32 dispensing the buffering agent into the anesthetic. A flange 220 on extends from a proximal end of the tubular plunger 201 to engage the rod 210 when advanced. Alternatively, a flange (not shown) may be positioned at or near the distal end of the tubular plunger 201 to contact the piston 42 to dispense the anesthetic. Barbs 222 at or near the distal end of the tubular plunger 201 may be configured to engage the piston 42 to prevent separation from the piston during aspiration. Alternatively, barbs (not shown) may extend from rod 210 to engage piston 42.

Having described the invention in detail, it will be apparent that modifications and variations are possible without departing from the scope of the invention defined in the appended claims. It is understood that embodiments of the invention may be used to deliver a two component drug in which the combination or mixing of the two components or two drugs is performed shortly before administration to the patient.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions, products, and methods without departing from the scope of the invention, it is intended that all matter contained in the above description and shown in the accompanying drawings shall be interpreted as illustrative and not in a limiting sense.

What is claimed is:

1. A syringe for dispensing anesthetic from a cartridge having an interior wall defining a hollow interior sized and shaped for receiving a dose of anesthetic, and a piston, the syringe comprising:
    a tubular plunger slidably received in the hollow interior of the tubular cartridge, said plunger having a hollow interior extending between a distal end shaped for engaging the piston and an open proximal end opposite the distal end; and
    a plunger rod slidably received in the hollow interior of the tubular plunger, the rod having a sharp distal end adapted to penetrate the piston, a proximal end, and a length extending between the distal end and the proximal end sized so that a delivery portion of the rod extends through the piston into the cartridge when the rod is driven through the piston, said delivery portion including a recess for receiving a buffering agent to reduce acidity of the dose of anesthetic.

2. A syringe as set forth in claim 1 wherein the recess is located in a side of the plunger rod.

3. A syringe as set forth in claim 2 wherein the recess is spaced from the sharp distal end of the plunger rod.

4. A syringe as set forth in claim 1 wherein the recess is spaced from the sharp distal end of the plunger rod.

5. A syringe as set forth in claim 1 wherein at least one of the rod and the plunger includes a detent and at least another of the rod and the plunger includes a corresponding opening for receiving the detent for retaining the relative position of the rod in the plunger.

6. A syringe as set forth in claim 5 wherein the rod includes a detent and the plunger includes a corresponding opening for receiving the detent for retaining the relative position of the rod in the plunger.

\* \* \* \* \*